US012121281B2

United States Patent
Shaari

(10) Patent No.: US 12,121,281 B2
(45) Date of Patent: Oct. 22, 2024

(54) SYSTEMS AND METHODS FOR CRYOGENIC TREATMENT OF HEADACHE

(71) Applicant: Christopher M. Shaari, Demarest, NJ (US)

(72) Inventor: Christopher M. Shaari, Demarest, NJ (US)

(*) Notice: Subject to any disclaimer, the term of this patent is extended or adjusted under 35 U.S.C. 154(b) by 751 days.

(21) Appl. No.: 16/988,224

(22) Filed: Aug. 7, 2020

(65) Prior Publication Data

US 2021/0038277 A1  Feb. 11, 2021

Related U.S. Application Data

(60) Provisional application No. 62/883,954, filed on Aug. 7, 2019.

(51) Int. Cl.
| | | |
|---|---|---|
| *A61B 18/02* | (2006.01) | |
| *A61B 18/00* | (2006.01) | |
| *A61M 25/00* | (2006.01) | |
| *A61M 25/10* | (2013.01) | |

(52) U.S. Cl.
CPC .......... *A61B 18/02* (2013.01); *A61B 18/0218* (2013.01); *A61M 25/10* (2013.01); *A61B 2018/0022* (2013.01); *A61B 2018/00327* (2013.01); *A61B 2018/00434* (2013.01); *A61B 2018/00577* (2013.01); *A61B 2018/0212* (2013.01); *A61M 2025/0001* (2013.01); *A61M 2210/0618* (2013.01)

(58) Field of Classification Search
None
See application file for complete search history.

(56) References Cited

U.S. PATENT DOCUMENTS

| | | | |
|---|---|---|---|
| 5,207,674 | A | 5/1993 | Hamilton |
| 5,669,903 | A | 9/1997 | O'Donnell |
| 7,758,571 | B2 | 7/2010 | Saadat |
| 8,666,498 | B2 | 3/2014 | Newman |
| 8,715,275 | B2 | 5/2014 | Burger et al. |

(Continued)

FOREIGN PATENT DOCUMENTS

| | | |
|---|---|---|
| CN | 87107517 A | 7/1988 |
| RU | 2185135 C | 7/2002 |

(Continued)

OTHER PUBLICATIONS

ClariFix® Cryotherapy, http://clarifix.com/for-physicians/, accessed Jun. 6, 2019.

(Continued)

*Primary Examiner* — Ronald Hupczey, Jr.
(74) *Attorney, Agent, or Firm* — Jon E. Gordon; Haug Partners LLP

(57) ABSTRACT

Methods and related systems treating headache and migraine. The method may include producing an injury to a nerve at an identified location of hypersensitivity; wherein the identified location is a location of nerve hypersensitivity. The identified location may be within the anterior or frontal aspect of a nasal cavity, corresponding to a location of the V1 branch of the trigeminal nerve. Producing an injury may comprise providing cryotherapy to the identified location. The cryotherapy is supplied by a chilled probe, a cryo-balloon, a nasal spray device, or a gel applicator.

11 Claims, 1 Drawing Sheet

(56) References Cited

U.S. PATENT DOCUMENTS

| | | |
|---|---|---|
| 10,028,781 B2 | 7/2018 | Saadat |
| 10,939,965 B1 * | 3/2021 | Saadat .................. A61B 34/20 |
| 2003/0088240 A1 | 5/2003 | Saadat |
| 2004/0215294 A1 | 10/2004 | Littrup et al. |
| 2006/0069385 A1 | 3/2006 | Lafontaine et al. |
| 2007/0129714 A1 | 6/2007 | Elkins et al. |
| 2008/0154254 A1 | 6/2008 | Burger et al. |
| 2008/0200910 A1 | 8/2008 | Burger et al. |
| 2009/0248001 A1 | 10/2009 | Burger et al. |
| 2009/0264876 A1 | 10/2009 | Roy et al. |
| 2009/0299357 A1 | 12/2009 | Zhou |
| 2010/0114191 A1 | 5/2010 | Newman |
| 2010/0274237 A1 | 10/2010 | Yamakawa et al. |
| 2011/0263921 A1 * | 10/2011 | Vrba ..................... A61B 18/18 604/93.01 |
| 2012/0253336 A1 | 10/2012 | Littrup et al. |
| 2012/0323227 A1 | 12/2012 | Wolf et al. |
| 2013/0184694 A1 | 7/2013 | Fourkas et al. |
| 2013/0184696 A1 | 7/2013 | Fourkas et al. |
| 2013/0190745 A1 | 7/2013 | Fourkas et al. |
| 2013/0289678 A1 | 10/2013 | Clark et al. |
| 2014/0228875 A1 | 8/2014 | Saadat |
| 2014/0276539 A1 | 9/2014 | Allison et al. |
| 2014/0316398 A1 | 10/2014 | Kelly et al. |
| 2015/0031946 A1 | 1/2015 | Saadat et al. |
| 2015/0088113 A1 | 3/2015 | Clark et al. |
| 2015/0126986 A1 | 5/2015 | Kelly et al. |
| 2015/0126988 A1 | 5/2015 | Hinton et al. |
| 2015/0164571 A1 | 6/2015 | Saadat |
| 2015/0320473 A1 | 11/2015 | Kalser et al. |
| 2016/0045277 A1 | 2/2016 | Lin et al. |
| 2016/0220294 A1 | 8/2016 | Babkin et al. |
| 2016/0262820 A1 | 9/2016 | Allison et al. |
| 2017/0049611 A1 | 2/2017 | Rosh Vora et al. |
| 2017/0231474 A1 | 8/2017 | Saadat |
| 2017/0348049 A1 | 12/2017 | Vrba et al. |
| 2018/0103994 A1 | 4/2018 | Fox et al. |
| 2018/0116705 A1 | 5/2018 | Lee et al. |
| 2018/0125560 A1 | 5/2018 | Saadat et al. |
| 2018/0303535 A1 | 10/2018 | Yu et al. |
| 2018/0344411 A1 | 12/2018 | Fahey et al. |
| 2019/0142494 A1 | 5/2019 | Cross et al. |

FOREIGN PATENT DOCUMENTS

| | | |
|---|---|---|
| RU | 2005126929 A | 2/2007 |
| RU | 2354348 C | 5/2009 |
| RU | 2371180 C | 10/2009 |
| RU | 2482811 C | 5/2013 |
| SU | 1602475 A | 10/1990 |
| SU | 1657159 A | 6/1991 |
| WO | WO 00/47118 A1 | 8/2000 |
| WO | WO 2018/142411 A1 | 8/2018 |
| WO | WO 2018/212840 A1 | 11/2018 |

OTHER PUBLICATIONS

Thien Phu Do et al., Myofascial trigger points in migraine and tension-type headache, Journal of Headache and Pain, Sep. 10, 2018, 19(84), BMC.

Norman Cook, Cryosurgery of Headache, Res. Clin. Stud. Headache, 1978, vol. 5, 86-101, Basel, Karger.

* cited by examiner

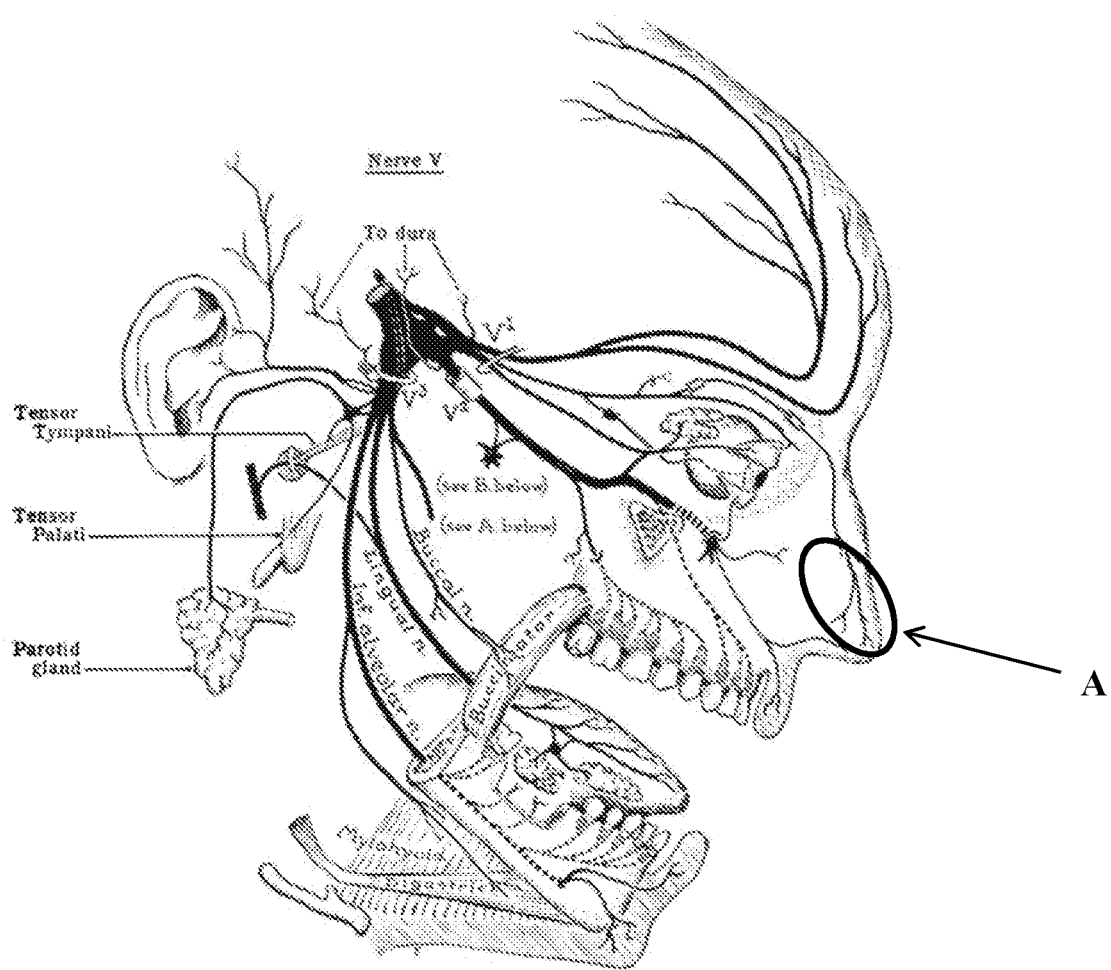

SYSTEMS AND METHODS FOR CRYOGENIC TREATMENT OF HEADACHE

CROSS-REFERENCE TO RELATED APPLICATION

This application claims the benefit of U.S. Provisional Patent Application No. 62/883,954, filed on Aug. 7, 2019, the entirety of which is herein incorporated by reference.

FIELD OF INVENTION

The present invention relates to systems and methods for treatment of headaches, and in particular, to systems and methods for cryogenically ablating nerve tissue for the treatment of migraine, headaches and sinus/facial pressure.

BACKGROUND

Headache pain, as well as pressure and/or throbbing, is one of the most common medical complaints. As many as 90 percent of all primary headaches fall under a few categories, including migraine, tension-type, and cluster headache. While episodic tension-type headache (TTH) is the most frequent headache type in population-based studies, migraine is the most common diagnosis in patients presenting to primary care physicians with headache.

Lifelong prevalence of headache is approximately 96%, with a female predominance. The global active prevalence of tension-type headache accounts for approximately 40% while migraine accounts for approximately 10%. Migraine is the third most prevalent disorder and the seventh highest cause of disability worldwide (see, Paul Rizzoli & William J. Mullally, *Headache,* 131 American Journal of Medicine 17, 24 (2018)). Migraines occur most commonly between the ages of 25 and 55 years and are 3 times more common in females. Despite the fact that it causes significant disability, migraine remains severely underdiagnosed and undertreated. In contrast, trigeminal autonomic cephalgias are rare compared with migraine and tension-type headache. The most common trigeminal autonomic cephalgia is cluster headache, with a population prevalence of 0.1% and a male/female ratio of 3.5-7:1. According to the International Classification of Headache Disorders (ICHD), headaches are classified into primary headaches, secondary headaches, and neuropathies and facial pains/other headaches. Primary headaches include migraine, tension-type headache, trigeminal autonomic cephalgia, and other primary disorders. Secondary headaches include headaches attributable to trauma/head injury, cranial disorders, and non-vascular intracranial disorders. See, https://ichd-3.org/classification-outline/.

More generally, headache pain can inflict personal suffering and impair overall quality of life. Moreover, individuals who suffer long-term chronic headache pain can be predisposed to suffer other illnesses; for example, depression is more common in people afflicted with recurring migraine or severe headaches as compared to those who do not suffer from recurring migraine or severe headaches.

In typical ER settings, topical lidocaine drops are administered into the nasal cavity using 8% lidocaine to anesthetize the sphenopalatine ganglion for acute control of migraine headache. However, such treatment is generally meant to be single use because of potential toxicities of lidocaine, in particular in relation to cardiac arrhythmias.

Additionally, the article *Myofascial trigger points in migraine and tension-type headache* (Do et al., *Myofascial trigger points in migraine and tension-type headache,* J. of Headache and Pain 19:84 (2018)) generally describes myofascial trigger points as hyperirritable locations in skeletal muscle that are associated with migraine and tension-type headaches, opining that ultrasound and EMG appear to be promising technologies for the identification of such locations.

Moreover, it is generally known in the prior art to attempt to treat headache utilizing cryogenic energy. For example, the article *Cryosurgery of Headache* (Norman Cook, *Cryosurgery of Headache,* 5 Res. Clin. Stud. Headache 86-101 (1978)) describes methods for cryogenically ablating nerves and arteries of the head, specifically in the sphenopalatine (SP) area. Such treatment specifically focused on freezing the arteries and ganglion of the SP area with a probe that is chilled to −120° C. to −160° C. However, the technique described often resulted in immediate reproduction of the headaches symptoms, such as nausea and vomiting, paresthesia, scotomata, hallucinations, and blurred vision. The technique was further found to be associated with an array of complications, including loss of smell, blurred vision, and diplopia.

The Rhinochill system is a transnasal cooling system that allows a patient to inhale cold air for about 20 minutes at 2° C., which has been shown to improve symptoms of migraine. However, multiple inhalations are required to cool the nasal cavity, and methods of implementing the system involve inhalation of a coolant placed through a catheter. Such a system results in adverse side effects, such as nosebleed, hypertension, pain, and coolant dripping from the nose.

U.S. Pat. No. 8,666,498 to Newmann relates to methods of treating headaches. According to one such method, an electrode probe is advanced to a target tissue (i.e., a stimulated nerve branch detected via EMG) and cryogenic energy is transmitted in order to stimulate and/or ablate tissue proximate to the electrode probe. The electrode probe may be placed percutaneously or placed directly on the skin surface.

Similarly, U.S. Pat. No. 8,715,275 to Burger at al. describes pain management systems and methods. Such systems and methods apply cooling with a percutaneously placed probe in order to remodel target tissue. According to exemplary embodiments, a needle probe is advanced through the skin to target tissue. A cooling fluid is then supplied to the target tissue via the probe. For example, the cooling fluid may be transmitted through the needle to a target nerve in order to reduce underlying pain.

The above prior art systems and methods have numerous drawbacks. Firstly, many of these systems and methods require percutaneous placement, which requires a high degree of precision and inflicts tissue damage during the procedure. Moreover, many of these systems and methods come with unwanted side effects and/or complications, due to the targeting of motor nerves and/or blood vessels that are often as debilitating as the headache. These systems and methods also typically lack the ability reliably localize the cause of the headache, such as an overactive nerve, and instead apply treatment to specific anatomical locations irrespective of the headache type or associated symptoms.

Thus, there is a need for better headache treatments that address the drawbacks of the prior art. Such systems and methods should be less invasive, better target the cause of the headache, and have reduced side effects/complications.

SUMMARY OF THE INVENTION

Headaches, facial pressure, nasal throbbing, and facial throbbing are very common symptoms in an otolaryngology practice. Often, these symptoms are construed to be of sinus origin, especially as perceived by the patient, but the traditional findings of sinusitis, such as inflammation and/or purulent nasal drainage, are not present. For example, common presenting symptoms from a patient include nasal or mid facial throbbing or pressure, forehead throbbing or pressure, and/or nasal or facial congestion located on one side or both sides of the face or head.

A diagnostic challenge arises when a nasal examination is inconsistent with the presented symptoms. For example, a patient with sinus pressure may not have any evidence of purulent nasal drainage on a nasal endoscopy yet they have symptoms of nasal congestion, facial pressure and headache. Differentiating a sinus from a non-sinus origin of symptoms can be particularly challenging, especially on a regular basis where routine diagnostic imaging such as a CAT scan, which would define the degree of inflammation, is infeasible and not indicated. It has been estimated that a substantial number of self-reported sinus headaches are in fact neurogenic in origin, with migraine or tension headache accounting for the majority of these symptoms.

According to aspects of the present invention, it has been found that during nasal endoscopy of a patient's being evaluated for sinus headache, certain regions of the nasal cavity are extraordinarily sensitive, a term known as allodynia, and seem to resemble the pain or pressure of a presenting symptom. Endoscopic examinations would often appear normal or with edema of the lining being very minimal, without evidence of active or chronic inflammation or infection. Although these regions of hypersensitivity are different among patients, they have been predominantly found to be located in the anterior or front aspect of the nasal cavity.

The distribution of the sensitivity has been found to most often be in regions of the nasal cavity, typically located on the anterior aspect of the lateral nasal wall just in front of the middle turbinate, on the medial and anterior nasal septal mucosa, or on the anterior superior aspect of the inferior turbinate. These locations have been found to be trigger spots for headache. These areas typically correspond to locations of the first division of the trigeminal nerve, known as the V1 branch, but can also correspond to locations of the V2 branch or other nerves. For example, extremely light touch with a blunt-tipped needle guided by a rigid nasal endoscope immediately activates headache symptoms at the location of the allodynia, with no specific regions of hypersensitivity present 2 to 3 mm away. Via application of topical anesthetic gel, either in the form of lidocaine or tetracaine gel, an almost immediate relief of symptoms of facial pressure, pain, and even fogginess can be seen. Often times the application of anesthetic gel can improve symptoms for periods of time, but some patients experience recurrent symptoms, specifically requesting application of topical anesthetic gel to break their symptoms. The location of the allodynia (i.e., nerve hypersensitivity) would be the same.

Accordingly, embodiments of the first aspect of the invention relate to methods for producing an injury to at least a portion of at least one nerve located in the anterior or front aspect of the nasal cavity in order to reduce the frequency and/or severity of headache or facial pressure. The method comprises producing an injury to a nerve at an identified location of hypersensitivity (i.e., an allodynia); wherein the identified location is a location of nerve hypersensitivity within an anterior or frontal aspect of a nasal canal.

According to preferred embodiments of the first aspect, the location of nerve hypersensitivity is identified by advancing a probe into the nasal cavity, touching different portions of the anterior or frontal aspect of the nasal cavity with the probe, and identifying which portion(s) of the anterior or frontal aspect of the nasal cavity are perceived by the patient as being hypersensitive. According to one preferred embodiment, the at least one nerve is the trigeminal nerve. According to most a preferred embodiment, identifying which portion(s) of the anterior or frontal aspect of the nasal cavity are perceived by the patient as being hypersensitive including determining which portion(s) of the V1 branch of the trigeminal nerve within the anterior or frontal aspect of the nasal cavity is/are perceived as hypersensitive.

According to embodiments of the first aspect, producing an injury to the nerve at the identified location of hypersensitivity includes producing an injury sufficient to disrupt nerve activity. According to embodiments, the injury is a second degree nerve injury (i.e., a grade 2 axonotmesis). The injury can be produced via mechanical stimulation or cryotherapy. According to preferred embodiments, the grade 2 axonotmesis is produced via application of cryotherapy. According to a most preferred embodiment, producing a grade 2 axonotmesis comprises applying cryotherapy with a temperature from between approximately −20° C. to −100° C.

According to certain embodiments, the method includes a further step of marking the location of hypersensitivity prior to the application of cryotherapy.

According to alternative embodiments, nerve activity is disrupted via the application of an anesthetic.

According to a second aspect of the invention, systems are disclosed for carrying out the methods of treating migraine and headache (e.g., reducing the frequency and/or severity of headache or facial pressure). The system may include a first device configured to locate a region of hypersensitivity within the anterior or frontal aspect of the nasal cavity and a second device configured to provide mechanical stimulation or cryotherapy to the identified location.

According to embodiments, the first device comprises a probe that is configured to be advanced into the anterior or frontal aspect of the nasal cavity. According to a preferred embodiment, the first device comprises an endoscope with an associated probe. The endoscope is configured to be placed within the nasal cavity such that the probe can be advanced into the anterior or frontal aspect of the nasal cavity such that the probe can make contact with areas of the anterior or frontal aspect of the nasal cavity corresponding to locations of sensory nerves located therein, and in particular to areas of the anterior or frontal aspect of the nasal cavity corresponding to locations of the V1 branch of the trigeminal nerve.

According to embodiments, the second device comprises a device configured to provide mechanical stimulation and/or cryotherapy to at least one area of the anterior or frontal aspect of the nasal cavity. According to embodiments for providing cryotherapy, the second device comprises a spray device configured to apply a cryogenic solution, a probe having a cooled tip, a cryo-balloon device, or a device configured to apply a cooled gel or hydrogel. According to embodiments for providing mechanical stimulation, the device comprises an expandable balloon, or a pressure gauge.

BRIEF DESCRIPTION OF THE DRAWINGS

The present disclosure will be further explained with reference to the attached drawing FIGURES, wherein like structures are referred to by like numerals throughout the several views. The drawing FIGURES shown are not necessarily to scale, with emphasis instead generally being placed upon illustrating the principles of the present disclosure, and some features may be exaggerated to show details of particular components. In addition, any measurements, specifications and the like shown in the drawing FIGURES, or described below, are intended to be illustrative, and not restrictive. Therefore, specific structural and functional details disclosed herein are not to be interpreted as limiting, but merely as a representative basis for teaching one skilled in the art to variously employ the systems and methods for cryogenic treatment of headaches.

FIG. 1 is a stylized illustration of the branching of the trigeminal nerve.

DETAILED DESCRIPTION

Detailed embodiments of methods and systems for treating headache and migraine are disclosed herein; however, it is to be understood that the disclosed embodiments are merely illustrative of systems and methods for treatment of headaches and migraine that may be embodied in various forms. In addition, each of the examples given in connection with the various embodiments of are intended to be illustrative, and not restrictive. And the specific structural and functional details disclosed herein are not to be interpreted as limiting, but merely as a representative basis for teaching one skilled in the art to variously employ systems and methods for treatment of headaches and migraine.

FIG. 1 illustrates the branching of the trigeminal nerve (i.e., the fifth cranial nerve or Nerve V) within the human head. The view shown in FIG. 1 and the descriptions thereof are not intended to be strictly anatomically accurate or complete, but rather illustrative, and provide a non-limiting illustration and description of certain features of the present invention. Further referring to FIG. 1, the trigeminal nerve includes three major branches (i.e., V1, V2, and V3). The V1 branch, also known as the opthalmic nerve, acts only as a sensory nerve (as opposed to a motor nerve or combination sensor and motor nerve) and innervates a number of frontal areas of the skull. A portion of the V1 branch, as indicated by area A in FIG. 1, innervates the anterior and frontal aspect of the nasal cavity.

According to embodiments of the present invention, it has been found that patients who experience migraine and tension-type headaches often have areas of hypersensitivity within the anterior or frontal aspect of the nasal cavity corresponding to hyperactivity of a portion of the V1 branch of the trigeminal nerve. Accordingly, methods and systems of the present invention are implemented to disrupt this hypersensitivity, which alleviates or eases the migraine and tension-type headache. Such systems and methods are further implemented to reduce the side effects patients experience from migraine and tension-type headaches, such as fogginess.

According to certain embodiments, methods for treating migraine and headache comprise producing an injury at an identified location of hypersensitivity. According to embodiments, the type of injury produced is intended to be sufficient to disrupt the nerve's activity, which in turn alleviates/treats the patient's migraine or headache. According to certain embodiments, the injury is a second degree nerve injury (i.e., a grade 2 axonotmesis). Such an injury does not result in permanent damage to the underlying nerve, but rather injures the nerve fibers so that they undergo reversible degeneration.

According to embodiments, the injury is produced via cryotherapy. According to preferred embodiments, the injury is produced via cryotherapy, the cryotherapy being in the form of applying a temperature from between approximately $-20°$ C. to $-100°$ C. to the identified nerve. According to a most preferred embodiment the temperature is approximately $-40°$ C. It has been found that cryotherapy in these temperature ranges is sufficient to induce the second degree nerve injury without creating a worsened rebound headache. Moreover, application of cryotherapy at temperatures below $-120°$ C. run the risk of causing irreversible damage, such as loss of smell, while temperatures above $-20°$ C. do not cause a sufficient injury to adequately disrupt the nerve. According to certain of these embodiments, the applied cryotherapy is localized to the area of hypersensitivity in order minimize peripheral tissue damage.

According to alternative embodiments, the injury is produced via mechanical stimulation. According to these embodiments, the mechanical stimulation is produced via expanding a balloon or via application of direct pressure within the nasal passage in order to crush the identified nerve. According to preferred alternative embodiments, the force applied is between approximately 0.25 and 12 atm. According to one illustrative embodiment, the force applied within the nasal passage is a pressure of approximately 2 atm.

According to embodiments, the identified location of hypersensitivity is a location of nerve hypersensitivity within an anterior or frontal aspect of a nasal canal. According to preferred embodiments, the location corresponds to a location of the V1 branch of the trigeminal nerve that is hypersensitive. According to certain preferred embodiments, this location is identified by advancing a probe into the nasal cavity, touching different portions of the anterior or frontal aspect of the nasal cavity with the probe, and identifying which portion(s) of the anterior or frontal aspect of the nasal cavity are perceived by the patient as being hypersensitive. According to one illustrative embodiment, this location is identified by advancing an endoscope, or similar device, into the nose of a patient. Subsequently, a probe, such as a blunt needle, can be advanced and brought into contact with the anterior and frontal aspects of the nasal cavity. The probe then makes contact with a plurality of areas within the anterior and frontal aspect of the nasal cavity of the patient until the patient indicates the location that the probe is contacting is a hypersensitive area.

According to embodiments, the method produces an injury to sensor nerve(s), and in particular to the V1 branch of the trigeminal, but not to motor nerves. This advantageously avoids the possibility of motor-based symptoms and side effects, such as droopy eye, vision loss, and loss of smell.

According to certain embodiments, systems for carrying out the above-described methods include a first device configured to locate a region of hypersensitivity within the anterior or frontal aspect of the nasal cavity and a second device configured to injure a nerve located at the region of hypersensitivity.

According to embodiments, the first device comprises a probe that is configured to be advanced into the anterior or frontal aspect of the nasal cavity. According to a preferred embodiment, the first device comprises an endoscope with an associated probe. The endoscope is configured to be placed within the nasal cavity such that the probe can be advanced adjacent to the endoscope (e.g., in a side channel or working channel) into the anterior or frontal aspect of the nasal cavity such that the probe can make contact with areas of the anterior or frontal aspect of the nasal cavity corresponding to locations of sensory nerves located therein, and in particular to areas of the anterior or frontal aspect of the nasal cavity corresponding to locations of the V1 branch of the trigeminal nerve.

According to embodiments, the second device comprises a device configured to provide mechanical stimulation and/or cryotherapy to at least one area of the anterior or frontal aspect of the nasal cavity. According to embodiments for providing cryotherapy, the second device comprises a spray device configured to apply a cryogenic solution, a probe having a cooled tip, a cryo-balloon device, or a device configured to apply a cooled gel or hydrogel.

According to preferred embodiments, the second device is a probe having a cooled tip. In these embodiments, the probe can take the form of a sheathed probe or an unsheathed probe. According to certain embodiments, the sheathed probe can be in the form of an advanceable probe with a cryogenically chilled tip. The probe is sheathed within an outer cannula, such as a syringe. The sheathed probe may be advanced into the nasal cavity via, for example, a working channel of an endoscope until the probe is located near the identified location of hypersensitivity. The probe is then advanced so that it extends out of the endoscope and is located proximate to the identified location of hypersensitivity. The probe is then advanced through the sheath, for example via a trigger or manual activation, such that the cryogenically chilled tip makes contact with the identified location of hypersensitivity. According to certain embodiments, the unsheathed probe can be in the form of a paddle-type device. The paddle-type device can include a handle with a detachable end. The detachable end can have a generally curved shape, such that it resembles a curved paddle. The handle can include a plurality of user-configurable joints, such that the handle can be precisely manipulated into and within the nasal cavity. The detachable end can be cryogenically frozen prior to use and attached to the handle when cryotherapy is to be applied. According to these embodiments, the probe advantageously allows for unilateral placement of cryotherapy, as opposed to bilateral application (when implementing a cryo-ballon or the like), avoiding regions of the sinonasal mucosa that are not hypersensitive, preventing aggravation of non-sensitized nerve areas and reducing the risks of undesired freezing of surrounding tissue. Further non-limiting illustrative examples of such a sheathed or unsheathed probe, include a shaft having a tip covered with an absorbent material or polymer (e.g., a cotton ball or polyurethane), the absorbent material having a cryogenic solution impregnated or otherwise applied therein.

According to embodiments for providing mechanical stimulation, the second device comprises an expandable balloon, or a pressure gauge. According to these embodiments, the second device is configured to be advanced into the nasal cavity and located proximate to the identified location of hypersensitivity. Direct pressure, via balloon expansion or direct pressure application, is then applied to the location of hypersensitivity in order to produce a crush-type, grade 2 injury. The pressure can be approximately 2 atm.

Although the above methods and related systems make specific reference to grade 2 injuries to the V1 branch of the trigeminal nerve, the present disclosure is not so limited. For example, the injury need not specifically be a grade 2 injury, but rather need only be an injury sufficient to disrupt nerve activity at the location of hypersensitivity. Moreover, as the embodiments illustrate, the area of hypersensitivity is often found to be in the anterior/frontal aspect of the nasal cavity. As FIG. 1 illustrates, the V2 branch (as well as other sensory nerves), are located within this region of the nasal cavity. The identified region of hypersensitivity may not specifically be located on the V1 branch, but instead may be located on the V2 branch (or other nerve). Thus, methods and systems of the present disclosure encompass treatment methods that disrupt any nerve (e.g., trigeminal nerve V1 branch, trigeminal nerve V2 branch, etc.) having a region of hyperactivity (i.e., the allodynia) within the anterior/frontal aspect of the nasal cavity.

EXAMPLES

Example #1

67-year-old female with right trigeminal neuralgia predominantly chronic throbbing over the left face, with chronic pressure, and with secondary diagnosis of migraine, was found to have hypersensitivity over the nasal septal swell body bilaterally worse on the patient's left side. Endoscopic palpation of the septal and nasal turbinate mucosa identified the site of hypersensitivity to be on the nasal septal swell body and the lateral wall superior to the inferior turbinate just anterior to the middle turbinate. The left side was more sensitive than the right. Topical tetracaine gel resulted in substantial resolution of her facial pressure. Cryotherapy was applied for 30 seconds to the region served by the upper division (V1 branch) of the trigeminal nerve. She was reevaluated approximately 3 months later and exhibited approximately 90% improvement of her symptoms with resolution of her throbbing sensation with persistent morning headache. This was found to be substantially reduced from her pretreatment state and possibly contributed by TMJ. Residual symptoms are mostly left temporal pain.

Example #2

54-year-old male with several years of right migraine symptoms, worsened with drops in barometric pressure, characterized by severe throbbing pain over and under the right orbit forehead lasting anywhere from 5-12 hours requires approximately 8 pills of Motrin to reduce migraine pain, was found to have a hypersensitive region on the right side of the lateral nasal wall just anterior to the right middle turbinate, and superior to the right inferior turbinate. The septal swell body was not hypersensitive. After 2 separate visits, confirming the site of hypersensitivity, cryotherapy was applied for 30 seconds. His postoperative course was uneventful, although there was initial rhinorrhea, followed by near complete resolution of his symptoms over the course of 5 months. He reported that the treatments were virtually life changing.

Example #3

44-year-old female with chronic bilateral tension headache with secondary migraine with symptoms of bilateral forehead and nasal bridge pressure and throbbing. She was dependent upon anti-inflammatories and was contemplating Botox injections for chronic migraine. She was identified to have increased sensitivity of the tissue just above the inferior turbinates bilaterally, as well as anterior to the middle turbinates, resembling the type of symptom that she developed when she had migraine and constant throbbing pressure. Topical tetracaine gel application deposited under direct endoscopic view resulted in substantial resolution of her symptoms. Subsequently she underwent bilateral cryotherapy. Her symptoms were markedly improved for approximately 1 month. She reported that the treatments were life changing and that she was able to wake up without a headache. At week 6 however, some of her symptoms seemed to recur.

Example #4

77-year-old female with right trigeminal cephalgia, predominant symptom of right orbital pain and pressure radiating from the right lateral bridge of her nose, with symptoms present for several months partially responsive to anti-inflammatories, was found to have a region of hypersensitivity at the anterior superior aspect of the right middle turbinate and anterior superior right lateral wall. The other regions of the anterior nasal cavity were not hypersensitive. Topical tetracaine gel immediately relieved her symptoms, followed by cryotherapy of this direct region. At 4 months after treatment she had complete relief of her symptoms.

Example #5

51-year-old female diagnosed with chronic tension headache, with right greater than left, but bilateral frontal pressure nasal throbbing extending to both sides of her forehead, despite decongestants and anti-inflammatories. She was found to have bilateral hypersensitivity at the region of the nasal swell body, as innervated by the first division of the trigeminal nerve. After confirming this site with resolution of her symptoms after topical tetracaine gel application, bilateral cryotherapy was performed and the patient had complete resolution of her chronic symptoms for 4 months. The treatment "got rid of daily headache and pressure."

The invention claimed is:

1. A method for treating migraine or headache, comprising:
   producing an injury to a nerve at an identified location of hypersensitivity,
   the identified location being a location such that stimulation at the location subjectively causes or aggravates one or more symptoms of migraine or headache;
   wherein the identified location is a location of nerve hypersensitivity within an anterior or frontal aspect of a nasal canal.

2. The method of claim 1, further comprising,
   identifying the location of nerve hypersensitivity,
   wherein identifying the location of nerve hypersensitivity, comprises:
   advancing a probe into a nasal cavity;
   touching different portions of the anterior or frontal aspect of the nasal cavity with the probe; and
   identifying which portion or portions of the anterior or frontal aspect of the nasal cavity are perceived as being hypersensitive.

3. The method of claim 2, wherein touching different portions of the anterior or frontal aspect of the nasal cavity with the probe comprising touching portions of the anterior or frontal aspect of the nasal cavity corresponding to locations of a trigeminal nerve.

4. The method of claim 3, wherein the locations of the trigeminal nerve comprise the V1 branch of the trigeminal nerve.

5. The method of claim 1, wherein producing the injury to the nerve at the identified location of hypersensitivity comprises producing an injury sufficient to disrupt nerve activity.

6. The method of claim 5, wherein producing the injury comprises a grade two axonotmesis.

7. The method of claim 5, wherein the injury is produced via mechanical stimulation or cryotherapy.

8. The method of claim 7, wherein the cryotherapy comprises applying cryotherapy to the identified location with a temperature between approximately −20° C. to −100° C.

9. The method of claim 7, wherein the mechanical stimulation comprises applying a pressure to the identified location, the pressure being between approximately 0.25 to 12 atm.

10. The method of claim 8, wherein the cryotherapy is applied with a device selected from the group consisting of:
    a spray device configured to apply a cryogenic solution;
    a probe having a cooled tip;
    a cryo-balloon device; and
    a device configured to apply a cooled gel or hydrogel.

11. The method of claim 9, wherein the mechanical stimulation is applied with a device selected from the group consisting of:
    an expandable balloon; and
    a pressure gauge.

* * * * *